United States Patent [19]
Bayer et al.

[11] 3,950,379
[45] Apr. 13, 1976

[54] 2-CYANO-DIPHENYL ETHERS

[75] Inventors: Horst O. Bayer, Levittown; Colin Swithenbank, Perkasie; Roy Y. Yih, Doylestown, all of Pa.

[73] Assignee: Rohm and Haas Company, Philadelphia, Pa.

[22] Filed: Aug. 19, 1974

[21] Appl. No.: 498,785

Related U.S. Application Data

[63] Continuation of Ser. No. 234,657, March 14, 1972, abandoned.

[52] U.S. Cl. ............... 260/465 F; 71/87; 71/90; 71/92; 71/93; 71/100; 71/105
[51] Int. Cl.² ............................. C07C 121/75
[58] Field of Search ..................... 260/465 F

[56]  References Cited
FOREIGN PATENTS OR APPLICATIONS
951,651   3/1964   United Kingdom

*Primary Examiner*—Elbert L. Roberts
*Assistant Examiner*—Dolph H. Torrence
*Attorney, Agent, or Firm*—William E. Lambert, III

[57] ABSTRACT

Compounds of the formula

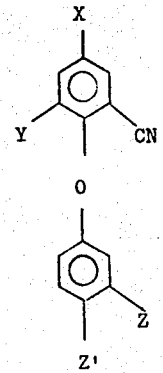

wherein
X is a halogen atom or a trihalomethyl group,
Y is a hydrogen atom, a halogen atom, a trihalomethyl group, or an alkyl group,
Z is a hydrogen atom, a halogen atom, a cyano group, a trihalomethyl group, an alkyl group, or an alkoxy group, and
Z' is a halogen atom, a cyano group, a trihalomethyl group, or, when X is a halogen atom, a nitro group, and compositions containing these compounds exhibit herbicidal activity.

7 Claims, No Drawings

2-CYANO-DIPHENYL ETHERS

This is a continuation of application Ser. No. 234,657 filed Mar. 14, 1972, and now abandoned.

This invention relates to novel compounds which show activity as herbicides, to novel herbicidal compositions which contain these compounds, and to new methods of controlling weeds with these herbicidal compositions.

Certain diphenyl ethers have been shown to be effective weed control agents. However, the herbicidal effectiveness of a given diphenyl ether cannot be predicted from an examination of the substituent groups attached to the phenyl rings in the ether, and often quite closely related compounds will have quite different weed control abilities. Various diphenyl ethers may have overlapping or complementary areas of activity or selectivity, and can thus be useful in combination to control a variety of weeds upon application of a single composition. Furthermore, the diphenyl ethers heretofore disclosed as herbicides are not completely effective. An ideal herbicide should give selective weed control, over the full growing season, with a single administration at low rates of application. It should be able to control all common weeds by killing them as the seed, the germinating seed, the seedling, and the growing plant. At the same time, the herbicide should not be phytotoxic to the crops to which it is applied and should decompose or otherwise be dissipated so as not to poison the soil permanently. The known diphenyl ether herbicides fall short of these ideals, and it would thus be desirable to have new herbicides which show even more selective control of undesirable plants among desirable crop plants or which complement the known diphenyl ethers in activity.

In accordance with the present invention, there is provided a new class of novel diphenyl ethers having the formula

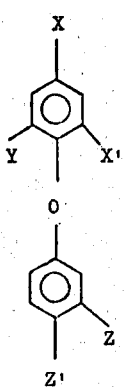

wherein
X is a halogen atom, preferably a fluorine atom or a chlorine atom, or a trihalomethyl group, preferably a trifluoromethyl group, X' is a cyano group, or, when X is a trifluoroalkyl group, a halogen atom, preferably a fluorine or chlorine atom, Y is a hydrogen atom, a halogen atom, preferably a fluorine atom or a chlorine atom, a trihalomethyl group, preferably a trifluoromethyl group, or a ($C_1$–$C_4$) alkyl group, preferably a methyl group, Z is a hydrogen atom, a halogen atom, preferably a fluorine atom or a chlorine atom, a cyano group, a trihalomethyl group, preferably a trifluoromethyl group, an alkyl group, preferably having 1 to 4 carbon atoms, or an alkoxy group, preferably having 1 to 6 carbon atoms, and Z' is a halogen atom, preferably a fluorine atom or a chlorine atom, a cyano group, a trihalomethyl group, preferably a trifluoromethyl group, or, when X is a halogen atom, a nitro group.

The alkyl portion of the alkyl-containing Y and Z substituents can have either a straight- or branched-chain or a cyclic spatial configuration. These novel compounds have been found to show unexpected activity as weed control agents. In a preferred embodiment of the invention, X is a trifluoromethyl group, X' is a cyano group, and Y and Z are hydrogen atoms.

Examples of the compounds of the invention embraced by Formula I include:
2-cyano-4-fluorophenyl-4-nitrophenyl ether,
2,4-dichloro-6-cyanophenyl-4-nitrophenyl ether,
2-chloro-6-cyano-α, α, α-trifluoro-p-tolyl-4-cyanophenyl ether,
2-cyano-α, α, α-trifluoro-p-tolyl-4-cyano-3-ethoxyphenyl ether,
2-cyano-α, α, α-trifluoro-p-tolyl-4-bromophenyl ether,
2-chloro-α, α, α-trifluoro-p-tolyl-3,4-dichlorophenyl ether,
2-cyano-α, α, α-trifluoro-p-tolyl-4-chloro-3-methylphenyl ether,
2-cyano-α, α, α-trifluoro-p-tolyl- α,α,α-trifluoro-p-tolyl ether,
4-bromo-2-cyanophenyl-4-nitro-α, α, α-trifluoro-p-tolyl ether,
2-cyano-α, α, α-trifluoro-p-tolyl-3-bromo-4-cyanophenyl ether,
4-chloro-2-cyanophenyl-3-cyano-4-nitrophenyl ether,
4-chloro-2-cyanophenyl-3,4-dichlorophenyl ether,
2-cyano-4-iodophenyl-4-nitrophenyl ether,
4-chloro-2-cyano-o-tolyl-4-chloro-m-tolyl ether,
2-cyano-α, α, α-trifluoro-p-tolyl-3-butyl-4-cyanophenyl ether, and the like.

The novel diphenyl ethers of the invention are useful both as preemergence and as postemergence herbicides. Preemergence herbicides are ordinarily used to treat the soil in which the desired crop is to be planted by application either before seeding, during seeding, or, as in most applications, after seeding and before the crop emerges. Postemergence herbicides are those which are applied after the plants have emerged and during their growth period.

Among the crops on which the diphenyl ethers of the invention can be advantageously employed are, for example, cotton, soybeans, peanuts, beans, peas, carrots, corn, and other cereal crops.

The diphenyl ethers of the invention are useful for controlling weeds in rice crops. When used in transplanted rice crops, the ethers can be applied either preemergence or postemergence to the weeds — that is, they can be applied to the transplanted rice plants and their growth medium either before the weed plants have emerged or while they are in their early stages of growth. The ethers can be applied to the growth medium either before or after the rice has been transplanted to that medium.

The diphenyl ethers of the invention can be applied in any amount which will give the required control of weeds. A preferred rate of application of the herbicides of the invention is from about 0.1 to about 12 pounds of the diphenyl ether per acre.

Under some conditions, the diphenyl ethers of the invention may be advantageously incorporated into the soil or other growth medium prior to planting a crop. This incorporation can be carried out by any convenient means, including by simple mixing with the soil, by applying the diphenyl ether to the surface of the soil and then disking or dragging into the soil to the desired depth, or by employing a liquid carrier to accomplish the necessary penetration and impregnation.

A diphenyl ether of the invention can be applied to the growth medium or to plants to be treated either by itself or, as is generally done, as a component in a herbicidal composition or formulation which also comprises an agronomically acceptable carrier. By agronomically acceptable carrier is meant any substance which can be used to dissolve, disperse, or diffuse a herbicidal compound in the composition without impairing the effectiveness of the herbicidal compound and which by itself has no detrimental effect on the soil, equipment, crops, or agronomic environment. Mixtures of the diphenyl ethers of the invention may also be used in any of these herbicidal formulations. The herbicidal compositions of the invention can be either solid or liquid formulations or solutions. For example, the diphenyl ethers can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in postemergence applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers Annual".

The diphenyl ether compounds of this invention can be dissolved in any appropriate solvent. Examples of solvents which are useful in the practice of this invention include alcohols, ketones, aromatic hydrocarbons, halogenated hydrocarbons, dimethylformamide, dioxane, dimethyl sulfoxide, and the like. Mixtures of these solvents can also be used. The concentration of the solution can vary from about 2% to about 98% with a preferred range being about 25% to about 75%.

For the preparation of emulsifiable concentrates, the diphenyl ether can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth slats or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates is usually about 10% to 60% and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to 98%, preferably about 40% to 75%. A dispersing agent can constitute about 0.5% to about 3% of the composition, and a wetting agent can constitute from about 0.1% to about 5% of the composition.

Dusts can be prepared by mixing the compounds of the invention with finely divided inert solids which may be organic or inorganic in nature. Materials useful for this purpose include, for example, botanical flours, silicas, silicates carbonates and clays. One convenient method of preparing a dust is to dilute a wettable powder with a finely divided carrier. Dust concentrates containing about 20% to 80% of the active ingredient are commonly made and are subsequently diluted to about 1% to 10% use concentration.

Granular formulations can be prepared by impregnating a solid such as granular fuller's earth, vermiculite, ground corn cobs, seed hulls, including bran or other grain-hulls, or similar material. A solution of one or more of the diphenyl ethers in a volatile organic solvent can be sprayed or mixed with the granular solid and the solvent then removed by evaporation. The granular material can have any suitable size, with a preferable size range of 16 to 60 mesh. The diphenyl ether will usually comprise about 2 to 15% of the granular formulation.

The diphenyl ethers of the invention can also be mixed with fertilizers or fertilizing materials before their application. In one type of solid fertilizing composition in which the diphenyl ethers can be used, particles of a fertilizer or fertilizing ingredients, such as ammonium sulfate, ammonium nitrate, or ammonium phosphate, can be coated with one or more of the ethers. The solid diphenyl ethers and solid fertilizing material can also be admixed in mixing or blending equipment, or they can be incorporated with fertilizers in granular formulations. Any relative proportion of diphenyl ether and fertilizer can be used which is suitable for the crops and weeds to be treated. The diphenyl ether will commonly be from about 5% to about 25% of the fertilizing composition. These compositions provide fertilizing materials which promote the rapid growth of desired plants, and at the same time control the growth of undesired plants.

The diphenyl ethers of the invention can be applied as herbicidal sprays by methods commonly employed, such as conventional high-gallonage hydraulic sprays, low gallonage sprays, airblast spray, aerial sprays and dusts. For low volume applications a solution of the compound is usually used. The dilution and rate of application will usually depend upon such factors as the type of equipment employed, the method of application, the area to be treated and the type and stage of development of the weeds.

For some applications, it may be desirable to add one or more other herbicides along with diphenyl ethers of the invention. Examples of other herbicides which can be incorporated to provide additional advantages and effectiveness include:

CARBOXYLIC ACIDS AND DERIVATIVES 2,3,6-trichlorobenzoic acid and its salts
2,3,5,6-tetrachlorobenzoic acid and its salts
2-methoxy-3,5,6-trichlorobenzoic acid and its salts
2-methoxy-3,6-dichlorobenzoic acid and its salts
2-methyl-3,6-dichlorobenzoic acid and its salts
2,3-dichloro-6-methylbenzoic acid and its salts
2,4-dichlorophenoxyacetic acid and its salts and esters
2,4,5-trichlorophenoxyacetic acid and its salts and esters 2-methyl-4-chlorophenoxyacetic acid and its salts and esters
2-(2,4,5-trichlorophenoxy)propionic acid and its salts and esters
2-(2,4-dichlorophenoxy)butyric acid and its salts and esters
4-(2-methyl-4-chlorophenoxy)butyric acid and its salts and esters
2,3,6-trichlorophenylacetic acid and its salts
3,6-endoxohexahydrophthalic acid
dimethyl 2,3,5,6-tetrachloroterephthalate
trichloroacetic acid and its salts
2,2-dichloropropionic acid and its salts
2,3-dichloroisobutyric acid and its salts

CARBAMIC ACID DERIVATIVES ethyl N,N-di(n-propyl)thiolcarbamate
propyl N,N-di(n-propyl)thiolcarbamate
ethyl N-ethyl-N-(n-butyl)thiolcarbamate
propyl N-ethyl-N-(n-butyl)thiolcarbamate
2-chloroallyl N,N-diethyldithiocarbamate
N-methyldithiocarbamic acid salts
ethyl 1-hexamethyleneiminecarbothiolate
isopropyl N-phenylcarbamate
isopropyl N-(m-chlorophenyl)carbamate
4-chloro-2-butynyl N-(m-chlorophenyl)carbamate
methyl N-(3,4-dichlorophenyl)carbamate

PHENOLS dinitro-o-(sec-butyl)phenol and its salts
pentachlorophenol and its salts

SUBSTITUTED UREAS 3-(3,4-dichlorophenyl)-1,1-dimethylurea
3-phenyl-1,1-dimethylurea
3-(3,4-dichlorophenyl)-3-methoxy-1,1-dimethylurea
3-(4-chlorophenyl)-3-methoxy-1,1-dimethylurea
3-(3,4-dichlorophenyl)-1-n-butyl-1-methylurea
3-(3,4-dichlorophenyl)-1-methoxy-1-methylurea
3-(4-chlorophenyl)-1-methoxy-1-methylurea
3-(3,4-dichlorophenyl)-1,1,3-trimethylurea
3-(3,4-dichlorophenyl)-1,1-diethylurea
dichloral urea

SUBSTITUTED TRIAZINES 2-chloro-4,6-bis(ethylamino)-s-triazine
2-chloro-4-ethylamino-6-isopropylamino-s-triazine
2-chloro-4,6-bis(methoxypropylamino)-s-triazine
2-methoxy-4,6-bis(isopropylamino)-s-triazine
2-chloro-4-ethylamino-6-(3-methoxypropylamino)-s-triazine
2-methylmercapto-4,6-bis(isopropylamino)-s-triazine
2-methylmercapto-4,6-bis(ethylamino)-s-triazine
2-methylmercapto-4-ethylamino-6-isopropylamino-s-triazine
2-chloro-4,6-bis(isopropylamino)-s-triazine
2-methoxy-4,6-bis(ethylamino)-s-triazine
2-methoxy-4-ethylamino-6-isopropylamino-s-triazine
2-methylmercapto-4-(2-methoxyethylamino)-6-isopropylamino-s-triazine

DIPHENYL ETHER DERIVATIVES 2,4-dichloro-4'-nitrodiphenyl ether
2,4,6-trichloro-4'-nitrodiphenyl ether
2,4-dichloro-6-fluoro-4'-nitrodiphenyl ether
3-methyl-4'-nitrodiphenyl ether
3,5-dimethyl-4'-nitrodiphenyl ether
2,4'-dinitro-4-trifluoromethyldiphenyl ether
2,4-dichloro-3'-methoxy-4'-nitrodiphenyl ether

ANILIDES

N-(3,4-dichlorophenyl)propionamide
N-(3,4-dichlorophenyl)methacrylamide
N-(3-chloro-4-methylphenyl)-2-methylpentanamide
N-(3,4-dichlorophenyl)trimethylacetamide
N-(3,4-dichlorophenyl)-$\alpha,\alpha$-dimethylvaleramide
N-isopropyl-N-phenylchloroacetamide
N-n-butoxymethyl-N-(2,6-diethylphenyl)-chloroacetamide
N-n-methoxymethyl-N-(2,6-diethylphenyl)-chloroacetamide

URACILS 5-bromo-3-s-butyl-6-methyluracil
5-bromo-3-cyclohexyl-1,6-dimethyluracil
3-cyclohexyl-5,6-trimethyleneuracil
5-bromo-3-isopropyl-6-methyluracil
3-tert-butyl-5-chloro-6-methyluracil

NITRILES 2,6-dichlorobenzonitrile
diphenylacetonitrile
3,5-dibromo-4-hydroxybenzonitrile
3,5-diiodo-4-hydroxybenzonitrile

OTHER ORGANIC HERBICIDES 2-chloro-N,N-diallylacetamide
N-(1,1-dimethyl-2-propynyl)-3,5-dichlorobenzamide maleic hydrazide
3-amino-1,2,4-triazole
monosodium methanearsonate
disodium methanearsonate
N,N-dimethyl-α,α-diphenylacetamide
N,N-di(n-propyl)-2,6-dinitro-4-trifluoromethylaniline
N,N-di(n-propyl)-2,6-dinitro-4-methylaniline
N,N-di(n-propyl)-2,6-dinitro-4-methylsulfonylaniline
O-(2,4-dichlorophenyl)-O-methyl-isopropylphosphoramidothioate
4-amino-3,5,6-trichloropicolinic acid
2,3-dichloro-1,4-naphthoquinone
di(methoxythiocarbonyl)disulfide
3-isopropyl-1H-2,1,3-benzothiadiazine-(4)3H-one-2,2-dioxide
6,7-dihydrodipyridol[1,2-a:2',1'-c]pyrazidinium salts
1,1'-dimethyl-4,4'-bipyridinium salts
3,4,5,6-tetrahydro-3,5-dimethyl-2-thio-2H-1,3,5-thiadiazine.

When mixtures of herbicides are employed, the relative proportions which are used will depend upon the crop to be treated and the degree of selectivity in weed control which is desired.

The diphenyl ethers of the invention or their precursors can be prepared by reacting a suitably substituted phenol, or the potassium or sodium salt of the phenol, with a suitably substituted halobenzene, such as a chloro or fluorobenzene, in the presence of an alkaline agent.

The following examples will further illustrate this invention but are not intended to limit it in any way. In Table I, typical diphenyl ethers of the invention are listed, along with their melting points and elemental analyses. A specific, illustrative preparation of the compound of Example 3 is described after Table I.

TABLE I

Diphenyl Ethers - Physical Data

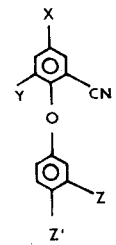

| Example No. | X | Y | Z | Z' | m.p. (b.p.)°C | | %C | %H | Analysis %N | %Cl | %F |
|---|---|---|---|---|---|---|---|---|---|---|---|
| 1 | F | H | H | NO₂ | 73–80 | found | 60.81 | 2.69 | 10.84 | | 7.32 |
| | | | | | | reqs. | 60.47 | 2.73 | 10.85 | 7.36 | |
| 2 | Cl | H | H | NO₂ | 96–97.5 | found | 57.06 | 2.69 | 9.91 | 12.89 | |
| | | | | | | reqs. | 56.84 | 2.57 | 10.20 | 12.91 | |
| 3 | CF₃ | H | H | Cl | 87.5–89 | found | 56.06 | 2.73 | 4.60 | 12.12 | 19.01 |
| | | | | | | reqs. | 56.48 | 2.37 | 4.71 | 11.91 | 19.15 |
| 4 | CF₃ | H | H | Br | 85–86 | found | 49.22 | 1.97 | 4.01 | 23.32* | 16.53 |
| | | | | | | reqs. | 49.15 | 2.06 | 4.09 | 23.36* | 16.66 |
| 5 | CF₃ | H | H | CN | 138–140.5 | found | 62.70 | 2.46 | 9.67 | | 19.70 |
| | | | | | | reqs. | 62.50 | 2.45 | 9.72 | | 19.78 |
| 6 | CF₃ | H | H | CF₃ | (110°/0.01mm) | found | 54.58 | 2.14 | 4.35 | | 34.42 |
| | | | | | | reqs. | 54.39 | 2.13 | 4.23 | | 34.42 |
| 7 | CF₃ | H | Cl | Cl | 60.5–61 | found | 50.50 | 1.85 | 4.06 | 21.40 | 17.12 |
| | | | | | | reqs. | 50.63 | 1.82 | 4.22 | 21.35 | 17.16 |

*%Br

EXAMPLE 3

Preparation of 2-cyano-α,α,α-trifluoro-p-tolyl-4-chlorophenylether

A solution of potassium hydroxide (1.96 g., 0.03 mole, 86.2% pure) and p-chlorophenol (3.86 g., 0.03 mole) in methanol (20 ml.) is stripped under reduced pressure. The residue is dissolved in sulpholane (60 ml), 4-chloro-3-cyano-α,α,α-trifluorotoluene (6.17 g., 0.03 mole) added, and the resulting solution heated at 120°–130°C for 5 hours. After cooling, the solution is pured into water and the precipitate filtered off, washed with water, and recrystallized from pentane/isopropanol to give 2-cyano-α,α,α-trifluoro-p-tolyl-4-chlorophenylether (3.3g., 37%) m.p. 87.5°–89°C.

EXAMPLES 8–17

Following the procedures of Examples 1 to 7, other diphenyl ethers of Formula I are prepared. Among the compounds which are prepared by these and other known procedures are:

2-chloro-α,α,α-trifluoro-p-tolyl-4-chlorophenyl ether,
2-chloro-α,α,α-trifluoro-p-tolyl-3,4-dichlorophenyl ether,
4-chloro-2-cyanophenyl-3-ethoxy-4-nitrophenyl ether,
2,4-dichloro-6-cyanophenyl-4-chlorophenyl ether,
2-cyano-α,α,α-trifluoro-p-tolyl-m-tolyl ether,
2-cyano-α,α,α-trifluoro-p-tolyl-4-chlorophenyl ether,
2-cyano-4-fluoro-o-tolyl-4-nitrophenyl ether, 2-cyano-α,α,α-trifluoro-p-tolyl-α,α,α-trifluoro-p-tolyl ether,
2-cyano-α,α,α-trifluoro-p-tolyl-4-bromophenyl ether, and
4-chloro-2-cyanophenyl-3-methoxyphenyl ether.

These diphenyl ethers have herbicidal properties.

It should be noted that the diphenyl ethers of the invention can be named correctly using different systems of nomenclature. For example, the diphenyl ether of Example 1 can also be named as 2-cyano-4-fluoro-4'-nitrodiphenyl ether. However, within the specification and claims of this invention the Chemical Abstracts system of nomenclature, as exemplified in Example 1–15, has been followed.

The following examples show the herbicidal properties of the diphenyl ethers of the invention.

EXAMPLE 18

This example shows the herbicidal activity of diphenyl ethers of the invention towards a number of common weeds. Using the procedure described below, diphenyl ethers were evaluated for control of the following weeds: At 10 pounds per acre:

Monocots barnyardgrass (Echinochloa crusgalli)
crabgrass (Digitaria spp.)
nutsedge (Cyperus esculentus)
wild oats (Avena fatua)

Dicots bindweed (Convolvulus arvensis)
curly dock (Rumex crispus)
velvetleaf (Abutilon theophrasti)
wild mustard (Brassica haber)
At 2 and 4 pounds per acre:

Monocots barnyardgrass (Echinochloa crusgalli)
crabgrass (Digitaria spp.)
downy brome (Bromus tectorum)
foxtail (Setaria faberii)
Johnsongrass (Sorghum halepense)
nutsedge (Cyperus esculentus)
quackgrass (Agropyron repens)
ryegrass (Lolium perenne)
wild oats (Avena fatua)
yellow millet (Panicum miliaceum)

Dicots bindweed (Convolvulus arvensis)
cocklebur (Xanthium pensylvanicum)
curly dock (Rumex crispus)
lambsquarters (Chenopodium album)
morningglory (Ipomoea purpurea)
pigweed (Amaranthus retroflexus)
smartweed (Polygonum pensylvanicum)
velvetleaf (Abutilon theophrasti)
wild carrot (Daucus carota)
wild mustard (Brassica haber)

The following test procedure is employed. Seeds of selected crops and weeds are planted in soil in flats. For preemergence tests, the flats are treated with the test compound immediately after the planting. For postemergence tests, the seeds are allowed to germinate, and after 2 weeks the flats are treated with the test compound. The compound to be evaluated is dissolved in acetone, diluted with water, and sprayed over the flats using a carrier volume equivalent to 50 gallons per acre at the rate of application (pounds per acre, lb/A.) specified in the tables. About 2 weeks after the application of the test compound, the state of growth of the plant is observed and the phytotoxic effect of the compound is evaluated. Table II gives the average percent control achieved by the test compounds in terms of the percent of the plants which are killed by the compounds.

TABLE II

| Compound of Example No. | lb./A. | HERBICIDAL ACTIVITY (% control) | | | | | |
|---|---|---|---|---|---|---|---|
| | | Preemergence | | | Postemergence | | |
| | | 10 | 4 | 2 | 10 | 4 | 2 |
| 1 | M* | 77 | 47 | | 95 | 44 | |
| | D* | 77 | 51 | | 100 | 58 | |
| 2 | M | 81 | 49 | | 95 | 44 | |
| | D | 95 | 55 | | 100 | 64 | |
| 3 | M | 10 | 59 | 65 | 17 | 9 | 27 |
| | D | 10 | 40 | 61 | 75 | 38 | 50 |
| 4 | M | 5 | 67 | 51 | 22 | 34 | 34 |
| | D | 0 | 37 | 34 | 85 | 56 | 50 |
| 5 | M | 70 | 44 | 42 | 25 | 11 | 48 |
| | D | 77 | 50 | 47 | 65 | 41 | 59 |
| 6 | M | 0 | | 34 | 70 | | 34 |
| | D | 10 | | 5 | 75 | | 49 |
| 7 | M | 0 | 66 | 56 | 40 | 36 | 36 |
| | D | 0 | 41 | 65 | 77 | 64 | 55 |

M* = Monocots; D = Dicots

It is to be understood that changes and variations may be made without departing from the spirit and scope of the invention as defined by the appended claims.

We claim:
1. A compound of the formula

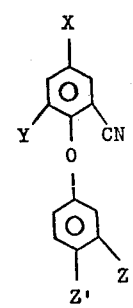

wherein

X is a halogen atom or a trifluoromethyl group,
Y is a hydrogen atom, a halogen atom, a trifluoromethyl group, or a ($C_1$–$C_4$) alkyl group,
Z is a hydrogen atom, a halogen atom, a cyano group, a trifluoromethyl group, a ($C_1$–$C_4$) alkyl group, or a ($C_1$–$C_6$) alkoxy group, and Z' is a halogen atom, a cyano group, a trifluoromethyl group, or, when X is a halogen atom, additionally a nitro group.

2. A compound according to claim 1 wherein Y is a hydrogen atom.

3. A compound according to claim 2 wherein X is a halogen atom.

4. A compound according to claim 3 wherein Z' is a nitro group.

5. A compound according to claim 4 wherein Z is a hydrogen atom.

6. A compound according to claim 2 wherein X is a trifluoromethyl group.

7. A compound according to claim 2 wherein Z' is a halogen atom.

* * * * *

UNITED STATES PATENT OFFICE
CERTIFICATE OF CORRECTION

Patent No. 3,950,379          Dated April 13, 1976

Inventor(s) H.O.Bayer, C.Swithenbank and R.Y.Yih

It is certified that error appears in the above-identified patent and that said Letters Patent are hereby corrected as shown below:

In column 4, line 14, "slats" should be --salts--.

In Table 1, under %Cl for Example 1, reqs "7.36" should be deleted.

In Table 1, under %F for Example 1, reqs "7.36" should be inserted.

In column 7, line 59, "contrpl" should be --control--.

Signed and Sealed this

Thirteenth Day of July 1976

[SEAL]

Attest:

RUTH C. MASON
*Attesting Officer*

C. MARSHALL DANN
*Commissioner of Patents and Trademarks*

UNITED STATES PATENT AND TRADEMARK OFFICE
Certificate

Patent No. 3,950,379                            Patented April 13, 1976

Horst O. Bayer, Colin Swithenbank & Roy Y. Yih

Application having been made by Horst O. Bayer, Colin Swithenbank & Roy Y. Yih, the inventors named in the patent above identified, and Rohm and Haas Co., Philadelphia, Pa., a corporation of Delaware, the assignee, for the issuance of a certificate under the provisions of Title 35, Section 256, of the United States Code, deleting the name of Roy Y. Yih as a joint inventor, and a showing and proof of facts satisfying the requirements of the said section having been submitted, it is this 13th day of Sept. 1983, certified that the name of the said Roy Y. Yih is hereby deleted from the said patent as a joint inventor with the said Horst O. Bayer & Colin Swithenbank.

Fred W. Sherling,
*Associate Solicitor*